(12) United States Patent
Brambilla et al.

(10) Patent No.: US 9,554,992 B2
(45) Date of Patent: *Jan. 31, 2017

(54) INHALATION PARTICLES COMPRISING A COMBINATION OF AN ANTICHOLINERGIC, A CORTICOSTEROID AND A BETA-ADRENERGIC

(71) Applicant: CHIESI FARMACEUTICI S.P.A., Parma (IT)

(72) Inventors: Gaetano Brambilla, Parma (IT); Michele Miozzi, Parma (IT); Timothy J Rouse, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/724,056

(22) Filed: May 28, 2015

(65) Prior Publication Data

US 2015/0352127 A1 Dec. 10, 2015

(30) Foreign Application Priority Data

Jun. 9, 2014 (EP) .................................... 14171644

(51) Int. Cl.
| | |
|---|---|
| *A61K 9/00* | (2006.01) |
| *A61K 31/40* | (2006.01) |
| *A61K 31/573* | (2006.01) |
| *A61K 31/167* | (2006.01) |
| *A61M 15/00* | (2006.01) |
| *A61M 16/20* | (2006.01) |
| *A61K 9/16* | (2006.01) |

(52) U.S. Cl.
CPC ............. *A61K 9/0075* (2013.01); *A61K 9/008* (2013.01); *A61K 9/1682* (2013.01); *A61K 31/167* (2013.01); *A61K 31/40* (2013.01); *A61K 31/573* (2013.01); *A61M 15/009* (2013.01); *A61M 15/0021* (2014.02); *A61M 15/0068* (2014.02); *A61M 16/20* (2013.01)

(58) Field of Classification Search
CPC .... A61K 31/167; A61K 31/40; A61K 31/573; A61K 9/0075; A61K 9/008; A61K 9/1682; A61M 15/0021; A61M 15/0068; A61M 15/009; A61M 16/20
See application file for complete search history.

(56) References Cited

U.S. PATENT DOCUMENTS 8,324,266 B2 * 12/2012 Vehring ................. A61K 9/008 424/45
2010/0269825 A1 * 10/2010 Cocconi ............... A61K 9/0075 128/203.15

(Continued)

OTHER PUBLICATIONS

Peter J. Barnes (2011) "Triple inhalers for obstructive airways disease: will they be useful?" Expert Review of Respiratory Medicine, 5:3, 297-300.*

(Continued)

*Primary Examiner* — Aradhana Sasan
(74) *Attorney, Agent, or Firm* — Oblon, McClelland, Maier & Neustadt, L.L.P.

(57) ABSTRACT

Microparticles comprising a combination of an anticholinergic, a beta$_2$-adrenoceptor agonist, and an inhaled corticosteroid are useful for the prevention and/or treatment of respiratory diseases.

24 Claims, 1 Drawing Sheet

A

B

(56) References Cited

U.S. PATENT DOCUMENTS

2010/0316724 A1* 12/2010 Whitfield ............. A61K 9/0075
424/489
2011/0150782 A1    6/2011 Bonelli et al.
2011/0262543 A1   10/2011 Cocconi et al.
2015/0017248 A1    1/2015 Pasquali et al.

OTHER PUBLICATIONS

M. Cazzola et al. "Long-acting bronchodilators in COPD: where are we now and where are we going?", Breathe, vol. 10, No. 2, pp. 110-120 (2014).
European Search Report issued in 14171644.9 on Aug. 22, 2014.

* cited by examiner

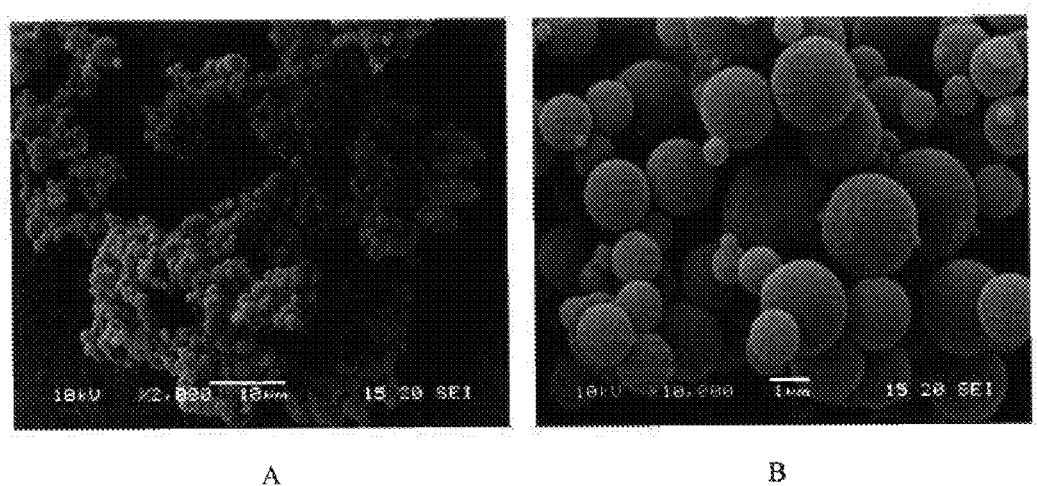

INHALATION PARTICLES COMPRISING A COMBINATION OF AN ANTICHOLINERGIC, A CORTICOSTEROID AND A BETA-ADRENERGIC

CROSS REFERENCES TO RELATED APPLICATIONS

This application claims priority to European Patent Application No. 14171644.9, filed on Jun. 9, 2014, which is incorporated herein by reference in its entirety.

BACKGROUND OF THE INVENTION

Field of the Invention

The present invention relates to particles comprising three active ingredients for administration by inhalation. In particular, the present invention relates to microparticles comprising a combination of an anticholinergic, a beta$_2$-adrenoceptor agonist, and an inhaled corticosteroid, processes for the preparation of such particles, and the use of such particles for the prevention and/or treatment of respiratory diseases.

Discussion of the Background

Respiratory diseases are a common and important cause of illness and death around the world. In fact, many people are affected by inflammatory and/or obstructive lung diseases, a category characterized by inflamed and easily collapsible airways, obstruction to airflow, problems of exhaling and frequent medical clinic visits and hospitalizations. Types of inflammatory and/or obstructive lung disease include asthma, bronchiectasis, bronchitis and chronic obstructive pulmonary disease (COPD).

In particular, chronic obstructive pulmonary disease (COPD) is a multi-component disease characterized by airflow limitation and airway inflammation. Exacerbations of COPD have a considerable impact on the quality of life, daily activities and general well-being of patients and are a great burden on the health system. Thus, the aims of COPD management include not only relieving symptoms and preventing disease progression but also preventing and treating exacerbations.

While available therapies improve clinical symptoms and decrease airway inflammation, they do not unequivocally slow long-term progression or address all disease components. With the burden of COPD continuing to increase, research into new and improved treatment strategies to optimize pharmacotherapy is ongoing.

Currently, there are several recommended classes of therapy for COPD, of which bronchodilators such as β$_2$-agonists and anticholinergics are the mainstay of symptom management in mild and moderate disease, prescribed on an as-needed basis for mild COPD and as a maintenance therapy for moderate COPD.

Said bronchodilators are efficiently administered by inhalation, thus increasing the therapeutic index and reducing side effects of the active material.

For the treatment of more severe COPD, guidelines recommend the addition of inhaled corticosteroids (ICSs) to long-acting bronchodilator therapy. Combinations of therapies have been investigated with a view to their complementary modes of action enabling multiple components of the disease to be addressed. Data from recent clinical trials indicate that triple therapy, combining an anticholinergic with an ICS and a long-acting β$_2$-agonist (LABA), may provide additional clinical benefits to those associated with each treatment alone in patients with moderate to severe COPD.

Furthermore, there is evidence suggesting synergistic actions of the LABA and ICS as long as both active ingredients are present at the same site of action, for example the small peripheral airways of the pulmonary tree. Without being limited by the theory, this might also occur if the anti-muscarinic drug is delivered at said site of action.

An interesting triple combination, presently under investigation, includes:

(i) formoterol, particularly its dihydrate fumarate salt (hereinafter indicated as FF), a long acting beta-2 adrenergic receptor agonist, currently used clinically in the treatment of bronchial asthma, COPD and related disorders;

(ii) rac-glycopyrronium bromide (hereinafter indicated as GB), an antimuscarinic drug recently approved for the maintenance treatment of COPD; and (iii) beclometasone dipropionate (hereinafter indicated as BDP) a potent anti-inflammatory corticosteroid, available under a wide number of brands for the prophylaxis and/or treatment of asthma and other respiratory disorders.

On the other hand, current combined inhalation products may be subjected to a great variability in the dose delivery of each active ingredient, which in turn may be perpetuated as a function of product storage conditions.

Hence, it would be advantageous to provide combination-particles for inhalation, and a process of preparation thereof, that will allow all the three active ingredients to be delivered without significant dose variations.

Furthermore, there is still a need of an improved therapeutic control of patients exhibiting respiratory diseases affecting the small peripheral airways.

Therefore, it would highly be advantageous to provide combination-particles, and a process of preparation thereof, whereby all the three active ingredients could simultaneously reach the distal tract of the respiratory tree, and hence improving small airways outcomes and associated control.

In the prior art, different approaches have been proposed for preparing particles incorporating a combination of two or more active ingredients. For example, WO 02/28377, WO 2010/097188, and WO 2013/021199, all of which are incorporated herein by reference in their entireties, disclose particles incorporating, inter alia, a LABA and an ICS. However, none of said documents disclose particles incorporating a combination of formoterol salts, beclometasone dipropionate and glycopyrronium salts. Furthermore, they are all silent about the problem of reaching the distal tract of the respiratory tree.

SUMMARY OF THE INVENTION

Accordingly, it is one object of the present invention to provide novel particles which comprise three active ingredients for administration by inhalation.

It is another object of the present invention to provide novel microparticles which comprise a combination of an anticholinergic, a beta$_2$-adrenoceptor agonist, and an inhaled corticosteroid.

It is another object of the present invention to provide novel processes for preparing such particles.

It is another object of the present invention to provide methods for the prevention and/or treatment of respiratory diseases by administering such particles.

These and other objects, which will become apparent during the following detailed description, have been achieved by the inventors' discovery of multicomponent microparticles for use in a pharmaceutical formulation for inhalation.

Thus, the present invention provides multicomponent microparticles, for use in a pharmaceutical formulation for inhalation, comprising a combination of beclometasone dipropionate, a pharmaceutically acceptable salt of formoterol, and a pharmaceutically acceptable salt of glycopyrronium in a ratio comprised between 35:15:45 and 94:1:5 w/w/w, whereby said microparticles are characterized by a shape factor comprised between 0.80 and 1.15, preferably between 0.90 and 1.10, more preferably between 0.95 and 1.05.

Preferably at least 90% of all the above microparticles have a volume diameter equal to or lower than 6.0 micron, preferably equal to or lower than 5.0 micron, and the volume median diameter of said particles is comprised between 1.0 and 3.0 micron, preferably between 1.2 and 2.5 micron, more preferably between 1.5 and 2.2 micron.

In a second aspect, the present invention provides pharmaceutical aerosol formulations for pressurized metered dose inhalers (pMDIs) comprising the above microparticles in suspension in a liquefied propellant gas.

In a third aspect, the present invention provides a pressurized metered dose inhaler (pMDI) comprising a canister filled with the aforementioned aerosol pharmaceutical formulation, and a metering valve for delivering a daily therapeutically effective dose of the active ingredients.

In a fourth aspect, the present invention provides a dry powder pharmaceutical formulation comprising the above microparticles and, optionally a carrier.

In a fifth aspect, the present invention provides a dry powder inhaler filled with the aforementioned dry powder formulation.

In a sixth aspect, the present invention is directed to a process for preparing the claimed microparticles, the process comprising the steps of:

a) preparing a solution of the three active ingredients in a pre-determined ratio in a suitable solvent mixture or any mixture thereof;

b) generating an aerosol from the solution of said three active ingredients; and c) drying the atomized droplets to yield the microparticles.

In a seventh aspect, the present invention relates to the claimed microparticles for use in the prevention and/or treatment of an inflammatory and/or obstructive airways disease such as asthma or chronic obstructive pulmonary disease (COPD).

In an eighth aspect, the present invention provides a method of preventing and/or treating an inflammatory and/or obstructive airways disease, such as asthma or chronic obstructive pulmonary disease (COPD), which comprises administering by inhalation of an effective amount of the microparticles of the invention.

In a ninth aspect, the present invention refers to the use of the claimed microparticles in the manufacture of a medicament for the prevention and/or treatment of an inflammatory and/or obstructive airways disease such as asthma or chronic obstructive pulmonary disease (COPD).

In a tenth aspect, the present invention refers to multicomponent microparticles for use in a pharmaceutical formulation for inhalation comprising a combination of beclometasone dipropionate, a pharmaceutically acceptable salt of formoterol, and a pharmaceutically acceptable salt of glycopyrronium in a ratio comprised between 35:15:45 and 94:1:5 w/w/w whereby said microparticles are characterized by a shape factor comprised between 0.80 and 1.15, preferably between 0.90 and 1.10, more preferably between 0.95 and 1.05, and are obtainable by a process comprising the steps of:

a) preparing a solution of the three active ingredients in a pre-determined ratio in a suitable solvent or any mixture thereof;

b) generating an aerosol from the solution of said three active ingredients; and c) drying the atomized droplets to yield the microparticles.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 A and B are SEM micrographs of the microparticles of the invention obtained by spray-drying.

DETAILED DESCRIPTION OF THE PREFERRED EMBODIMENTS

The terms "muscarinic receptor antagonists," "antimuscarinic drugs" and "anticholinergic drugs" can be used synonymously.

The term "pharmaceutically acceptable salt of glycopyrronium" refers to a salt of the compound 3-[(cyclopentylhydroxyphenylacetyl)oxy]-1,1-dimethylpyrrolidinium.

The term "pharmaceutically acceptable salt of formoterol" refers to a salt of the compound 2'-hydroxy-5'-[(RS)-1-hydroxy-2 {[(RS)-p-methoxy-α-methylphenethyl]amino}ethyl]formanilide.

The term "beclometasone dipropionate" refers to the compound (8S,9R,10S,11S,13S,14S,16S,17R)-9-chloro-11-hydroxy-10,13,16-trimethyl-3-oxo-17-[2-(propionyloxy) acetyl]-6,7,8,9,10,11,12,13,14,15,16,17-dodecahydro-3H-cyclopenta[a]phenanthren-17-yl propionate.

The term "pharmaceutically acceptable salt" comprises inorganic and organic salts. Examples of organic salts may include formate, acetate, trifluoroacetate, propionate, butyrate, lactate, citrate, tartrate, malate, maleate, succinate, methanesulfonate, benzenesulfonate, xinafoate, pamoate, and benzoate. Examples of inorganic salts may include fluoride chloride, bromide, iodide, phosphate, nitrate, and sulfate.

The term "solvent" is used to mean the medium in which the active ingredients are dissolved, while the term "antisolvent" is used to mean the medium in which crystallization takes place.

The term "multicomponent particle" refers to the smallest discrete single particle comprising a combination of three active ingredients. Said single particle is engineered in a spherical or almost spherical form.

The term "micronized" refers to a substance having a size of few microns.

The term "coarse" refers to a substance having a size of one or few hundred microns.

In general terms, the particle size of particles is quantified by measuring a characteristic equivalent sphere diameter, known as volume diameter, by laser diffraction.

The particle size can also be quantified by measuring the mass diameter by means of suitable known instrument such as, for instance, the sieve analyzer.

The volume diameter (VD) is related to the mass diameter (MD) by the density of the particles (assuming a size independent density for the particles).

In the present application, the particle size of the active ingredients and of the fraction of fine particles is expressed in terms of volume diameter, while that of the coarse particles is expressed in terms of mass diameter.

The particles have a normal (Gaussian) distribution which is defined in terms of the volume or mass median diameter (VMD or MMD) which corresponds to the volume or mass diameter of 50 percent by weight of the particles, and, optionally, in terms of volume or mass diameter of 10% and 90% of the particles, respectively.

Another common approach to define the particle size distribution is to cite three values: i) the median diameter d(0.5) which is the diameter where 50% of the distribution is above and 50% is below; ii) d(0.9), where 90% of the distribution is below this value; iii) d(0.1), where 10% of the distribution is below this value.

The span is the width of the distribution based on the 10%, 50% and 90% quantile and is calculated according to the formula:

$$\text{Span} = \frac{D[v, 0.9] - D[v, 0.1]}{D[v, 0.5]}$$

In general terms, particles having the same or a similar VMD or MMD can have a different particle size distribution, and in particular a different width of the Gaussian distribution as represented by the d(0.1) and d(0.9) values.

Upon aerosolization, the particle size is expressed as mass aerodynamic diameter (MAD), while the particle size distribution is expressed in terms of mass median aerodynamic diameter (MMAD) and Geometric Standard Deviation (GSD). The MAD indicates the capability of the particles of being transported suspended in an air stream. The MMAD corresponds to the mass aerodynamic diameter of 50 percent by weight of the particles.

In the final formulation, the particle size of the microparticles of the present invention can be determined by scanning electron microscopy or other methods known to the skilled person in the art.

The term "synergistic" means that the activity of the active ingredients is more than would be expected by summing their respective individual activities in a given assay.

The term "interactive or ordered mixture" refers to a powder formulation for inhalation comprising a pharmacologically-inert physiologically acceptable carrier substance, to which the micronized active compound particles are bonded by adhesion in order to achieve and to maintain a suitable mixed material, i.e. homogeneity of the mixture.

The term "relatively highly fissured surface" means a surface on which there are clefts and valleys and other recessed regions, referred to herein collectively as fissures.

The term "hard pellets" refers to spherical or semispherical units whose core is made of coarse excipient particles.

The term "spheronization" refers to the process of rounding off of the particles which occurs during the treatment.

The term "good flowability" refers to a formulation that is easy handled during the manufacturing process and is able to ensure an accurate and reproducible delivering of the therapeutically effective dose.

Flow characteristics can be evaluated by different tests such as angle of repose, Can's index, Hausner ratio or flow rate through an orifice.

In the context of the present application the flow properties were tested by measuring the flow rate through an orifice according to the method described in the European Pharmacopeia (Eur. Ph.) 7.3, $7^{th}$ Edition, which is incorporated herein by reference in its entirety.

The expression "good homogeneity" refers to a powder wherein, upon mixing, the uniformity of distribution of a component, expressed as coefficient of variation (CV) also known as relative standard deviation (RSD), is less than 5.0%. It is usually determined according to known methods, for instance by taking samples from different parts of the powder and testing the component by HPLC or other equivalent analytical methods.

The expression "respirable fraction" refers to an index of the percentage of active particles which would reach the lungs in a patient.

The respirable fraction is evaluated using a suitable in vitro apparatus such as Andersen Cascade Impactor (ACI), Multi Stage Liquid Impinger (MLSI), or Next Generation Impactor (NGI), according to procedures reported in common Pharmacopoeias, in particular in the European Pharmacopeia (Eur. Ph.) 7.3, $7^{th}$ Edition, which is incorporated herein by reference in its entirety. It is calculated by the percentage ratio of the fine particle mass (formerly fine particle dose) to the delivered dose.

The delivered dose is calculated from the cumulative deposition in the apparatus, while the fine particle mass is calculated from the deposition of particles having a diameter <5.0 micron.

In the context of the present invention, the formulation is defined as an "extrafine" formulation when it is capable of delivering a fraction of particles having a particle size equal or less than 2.0 micron equal to or higher than 20%, preferably equal to or higher than 25%, more preferably equal to or higher than 30%, and/or it is capable of delivering a fraction of particles having a particle size equal or less than 1.0 micron equal to or higher than 10%.

The expression "chemically stable" refers to an active ingredient that, upon storage of the microparticles, meets the requirements of the EMEA Guideline CPMP/QWP/122/02 referring to 'Stability Testing of Existing Active Substances and Related Finished Products', which is incorporated herein by reference in its entirety.

The expression "physically stable" refers to microparticles which exhibit substantially no change in morphology, no transition from amorphous to crystalline state or vice versa, no growth in particle size during storage in suitable containers for at least one month at room temperature and 60% relative humidity, as determined according to methods known to the skilled person in the art.

The expression "good constancy of the active ingredients ratio" means that the three active ingredients, after delivery of a single therapeutic dose, maintain substantially the same ratio as the pre-determined ratio of said two active ingredient in the formulation, i.e. that the relative standard deviation (RSD) of the ratio of the amounts of drugs measured in an in vitro apparatus such as NGI is less is less than 15%, preferably less than 10%.

The term "prevention" means an approach for reducing the risk of onset of a disease.

The term "treatment" means an approach for obtaining beneficial or desired results, including clinical results. Beneficial or desired clinical results can include, but are not limited to, alleviation or amelioration of one or more symptoms or conditions, diminishment of the extent of disease, stabilized (i.e. not worsening) state of the disease, preventing spread of the disease, delay or slowing of disease progression, amelioration or palliation of the disease state, and remission (whether partial or total), whether detectable or undetectable. The term can also mean prolonging survival as compared to expected survival if not receiving treatment.

According to the Global Initiative for Asthma (GINA), which is incorporated herein by reference in its entirety, "uncontrolled persistent asthma" is defined as a form characterized by daily symptoms, frequent exacerbations, frequent nocturnal asthma symptoms, limitation of physical activities, forced expiratory volume in one second ($FEV_1$) equal to or less than 80% predicted and with a variability higher than 30%. According to the Global Initiative for Asthma (GINA) guidelines 2014, which is incorporated herein by reference in its entirety, "partially uncontrolled asthma" is defined as a form characterized by less than twice a week daily symptoms, less than twice a month, nocturnal asthma symptoms, and a forced expiratory volume in one second ($FEV_1$) higher than 80% with a variability comprised between 20 and 30%.

According to the Global initiative for chronic Obstructive Pulmonary Disease (GOLD) guidelines, which is incorporated herein by reference in its entirety, "severe COPD" is a form characterized by a ratio between $FEV_1$ and the Forced Vital Capacity (FVC) lower than 0.7 and $FEV_1$ between 30% and 50% predicted. The very severe form is further characterized by chronic respiratory failure.

"Single therapeutically effective dose" means the quantity of active ingredient administered at one time by inhalation upon actuation of the inhaler. Said dose may be delivered in one or more actuations, preferably one actuation (shot) of the inhaler. Actuation refers to the release of active ingredients from the device by a single activation (e.g. mechanical or breath).

The expression "water insoluble or poorly water soluble" are used with reference to the solubility in water as defined in the European Pharmacopoeia Ed. $4^{th}$, 2003, page 2891, which is incorporated herein by reference in its entirety.

The term "UPLC-PDA" refers to an ULTRA-Performance Liquid Chromatography instrument coupled with a Photodiode Array detector.

The present invention is directed to multicomponent microparticles for use in a pharmaceutical formulation for inhalation comprising a combination of beclometasone dipropionate, a pharmaceutically acceptable salt of formoterol, and a pharmaceutically acceptable salt of glycopyrronium.

Formoterol may be present in the form of any pharmaceutically acceptable salt and/or solvate form thereof, preferably in the form of dihydrate fumarate salt.

Glycopyrronium may be used in the form of any of the pure enantiomers or diastereoisomers or any combination thereof in practicing the present invention. In a preferred embodiment, the (3S,2'R), (3R,2'S) 1:1 racemic mixture is used, also known as rac-glycopyrronium. Said active ingredient may be present in the form of any pharmaceutically acceptable salts and/or solvate form thereof, preferably in the form of bromide or monohydrate chloride, more preferably in form of bromide salt.

Beclometasone dipropionate may be anhydrous or present in the form of a monohydrate.

The ratio by weight in which the three active ingredients, e.g. beclometasone dipropionate, a pharmaceutically acceptable salt of formoterol, and a pharmaceutically acceptable salt of glycopyrronium, are present in the microparticles is pre-determined in such a way as to deliver the desired single therapeutically effective dose of each active ingredient.

As follows, the ratio by weight among the three active ingredients is given by making reference to the anhydrous form of beclometasone dipropionate (BDP), to the dihydrate fumarate salt of formoterol (FF), and to the bromide salt of glycopyrronium (GB).

Advantageously, said ratio of the anhydrous form of beclometasone dipropionate (BDP), to the dihydrate fumarate salt of formoterol (FF), and to the bromide salt of glycopyrronium (GB) is comprised between 35:15:45 and 94:1:5 w/w/w, preferably between 70:10:20 and 92:2:6, more preferably between 75:10:15 and 85:5:10.

Examples of ratios according to the present invention are:
84.4:5.1:10.5 w/w/w to deliver 100 microg BDP, 6 microg FF, and 12.5 microg GB;
91.5:2.7:5.8 w/w/w to deliver 200 microg BDP, 6 microg FF, and 12.5 GB;
73.0:8.8:18.2 w/w/w to deliver 50 microg BDP, 6 microg FF, and 12.5 GB;
80.3:9.6:10.1 w/w/w to deliver 100 microg BDP, 12 microg FF, and 12.5 microg GB;
89.1:5.3:5.6 w/w/w to deliver 200 microg BDP, 12 microg FF, and 12.5 microg GB;
72.7:4.4:22.9 to deliver 200 microg BDP, 12 microg FF and 63 microg GB; and
59.2:3.5:37.3 w/w/w to deliver 100 microg BDP, 6 microg FF, and 63 microg GB.

In a preferred embodiment, the three active ingredients are present in a ratio of 84.4:5.1:10.5, or 91.5:2.7:5.7, or 73.0:8.8:18.2 w/w/w, more preferably of 84.4:5.1:10.5 w/w/w.

The microparticles of the present invention are chemically stable and physical stable.

In fact, upon storage in suitable containers, the microparticles of the present invention turned out to be stable for at least one month at room temperature and 60% relative humidity, and for at least five months in refrigerated conditions.

Upon their delivery, they exhibit a good constancy of the active ingredients ratio and give rise to a high fraction of extrafine particles indicating that could be suitable for the prevention and/or treatment of the diseases affecting the distal tract of the respiratory tree.

Furthermore, the microparticles of the present invention have a uniform and almost regular spherical shape, exhibiting more homogeneous forces of adhesion among the whole powder which are in turn associated with the improved DPI performance.

The shape factor is used to characterize the shape of the microparticles.

Accordingly, the microparticles of the present invention are characterized by a shape factor comprised between 0.80 and 1.15, preferably between 0.90 and 1.10, more preferably between 0.95 and 1.05.

The shape factor may be determined according to the following equation reported in S. Kumar, et al., "*Influence of metal powder shape on drag coefficient in a spray jet*," Curr. Appl. Phys., 2009, 9, 678-682 (Kumar et al.), which is incorporated herein by reference in its entirety:

$$SF=1/RN$$

wherein:
RN indicates the roundness of the particle and is calculated by applying the following formula:

$$RN=p^2/4\pi A$$

wherein p and A are the mean perimeter and area values, respectively, of ten spherical particles as measured from Scanning electron microscopy (SEM) images.

Alternatively, the mean perimeter and area may be measured by an optical microscope.

In Kumar et al., it is reported that the shape factors (SF) of circle is 1.00. It is also reported that deviation from unity leads to irregularity of the particle, but particles with a SF value higher than 0.8 can be considered having a spherical shape.

Scanning electron microscopy (SEM) or optical microscopy may also be used to qualitatively appreciate the characteristics of the powder microparticles of the present invention such as particles shape and their surface morphology.

Since the microparticles of the present invention should be administered to the lungs by inhalation, at least 90% of them should have a volume diameter equal to or lower than 6 microns.

On the other hand, it is well known that most of the available therapeutic approaches tend to be associated with a poor therapeutic control of individuals exhibiting respiratory diseases affecting the small airways such as the small airways asthma phenotype.

By means of microparticles of the present invention, all three of the active ingredients could simultaneously reach the distal tract of the respiratory tree whereby they could act synergistically and improve small airways outcomes and associated control.

In fact, said microparticles are characterized by a selected, narrow, and well defined particle size distribution wherein the at least 90% of all of them have a volume diameter lower than 6.0 microns, preferably equal to or lower than 5.0 microns, more preferably equal to or lower than 4.5 microns, even more preferably equal to or lower than 4.0 microns, and their volume median diameter is from 1.0 to 3.0 microns, preferably from 1.2 to 2.5 microns, more preferably from 1.5 to 2.2 microns.

Advantageously, no more than 10% of said microparticles have a diameter lower than 0.2 microns, preferably equal to or lower than 0.5 microns, more preferably equal to or lower than 0.6 microns.

It follows that the width of the particle size distribution of the particles of each active ingredient, expressed as a span, should be advantageously comprised between 1.2 and 3.6, more advantageously between 1.0 and 3.5, preferably between 1.3 and 3.0, more preferably between 1.6 and 2.0. According to Chew, et al., J. Pharm. Pharmaceut. Sci. 2002, 5, 162-168, which is incorporated herein by reference in its entirety, the span corresponds to $[d(v, 0.9)-d(v,0.1)]/d(v, 0.5)$.

The size of the microparticles is determined by measuring the characteristic equivalent sphere diameter, known as volume diameter, by laser diffraction. In the reported examples, the volume diameter has been determined using a Malvern apparatus. However, other equivalent apparatus may be used by the skilled person in the art.

When determined by the Brunauer-Emmett-Teller (BET) nitrogen adsorption method according to a procedure known to the skilled person in the art, the Specific Surface Area of the microparticles of the present invention shall be from 1.5 to 5.0 $m^2/g$, preferably from 2.0 to 4.0 $m^2/g$.

The cohesion and adhesion forces of the microparticles of the present invention were also assessed by atomic force microscopy (AFM) according to the experimental procedure reported in Example 2. A bed of alpha-lactose monohydrate powder was used to perform the measurements. This powder bed represents a heterogeneous surface in which the contact area for adhesion is highly variable. The contact area in turn is a dominant factor in determining the force of interaction. Comparison of the obtained adhesion and cohesion forces suggests that there is no statistical difference in the magnitude of the interaction of the microparticles of the present invention with themselves or with the lactose powder. In sharp contrast, common micronized active ingredients are either strongly adhesive or cohesive. In virtue of said properties, the microparticles of the present invention may exhibit improved dispersion when formulated as interactive ordered mixtures with excipient particles of lactose as a carrier. In fact, they would be less prone to give rise to the formation of stable agglomerates like common micronised active ingredients.

In a further aspect, the present invention provides a process for the production of the microparticles of the present invention comprising the steps of:

a) preparing a solution of the three active ingredients in a pre-determined ratio in a suitable solvent or any mixture thereof;

b) generating an aerosol from the solution of said three active ingredients;

c) drying the atomized droplets to yield the microparticles; and d) isolating and collecting the produced microparticles.

As a result of said process, the microparticles are obtained as a completely amorphous powder in that each active ingredient is present in an amorphous form.

As far as the step a) is concerned, the choice of the solvent is critical as, besides having a high solubilizing capacity for the three active ingredients, it should also have a suitable degree of volatility and diffusion characteristics within the atomized droplets. These properties indeed significantly affect the particle size distribution of the resulting microparticles.

The skilled person in the art should be capable of choosing the solvent in relation to the desired particle size distribution.

For instance, solvents selected from the group consisting of water, ethanol, methanol, acetonitrile and DMSO, alone or in any mixture thereof in any ratio, may be used.

In a preferred embodiment of the present invention, the solvent may be a mixture of ethanol:water in a ratio ranging from 85:15 to 95:5 v/v, preferably 90:10 v/v.

For step b), any aerosol based atomization system may be used for the generation of the aerosol. Various systems for generating aerosols are well-known. The aerosol may, for example, be generated from the desired substances dissolved in a suitable solvent by electrohydrodynamic spraying, high air pressure atomiser or other aerosol generators including pneumatic systems, rotary (spinning-top) systems, spray nozzles, nebulizers, propellant evaporation systems, piezoelectric transducers, and ultrasonic transducers.

In a preferred embodiment, the microparticles are prepared by spray-drying. In this case, the solution of step a) is introduced into the drying chamber of a spray-drier through an atomizing device to form droplets, and the atomized droplets are dried by introducing a stream of pre-heated drying gas into said drying chamber.

Any commercially available spray-drier may be advantageously used.

The skilled person in the art shall properly adjust the conditions of the aerosol generation such as the temperature of the solution, the solution flow rate and the pressure of the carrier gas, in relation with the desired particle size distribution of the microparticles and the size of the batch.

In a particular embodiment of the present invention, it might be preferred to obtain partially amorphous or crystalline microparticles in that at least one of the active ingredients is in crystalline form.

In this case, in step d) of the aforementioned process of preparation, the microparticles are collected in a vessel containing an anti-solvent for all the three active ingredients; then, a high intensity ultrasound is applied to change the morphology of the microparticles and induce the crystallization of at least one of the three active ingredients present in the microparticle.

The anti-sovent may advantageously selected form the group consisting of n-heptane, cyclohexane, and fluorinated hydrocarbons, such as perfluorodecalin.

Further details about the conditions to induce crystallization are disclosed in WO 2010/007447 and WO 2010/097188, which are incorporated herein by reference in their entireties.

The partially amorphous or crystalline microparticles could be further isolated and collected according to methods known to the skilled person in the art.

When the microparticles of the present invention comprising formoterol fumarate, beclometasone dipropionate, and glycopyrronium bromide are isolated as an amorphous powder, they contain all the three active ingredients in the anhydrous form.

On the contrary, when said microparticles are isolated as partially amorphous or crystalline powder, they might contain formoterol fumarate as a dihydrate form and beclometasone dipropionate as a monohydrate form.

The amorphicity and/or crystallinity and, extent thereof, may be determined using X-ray powder diffraction or other techniques known to the skilled person such as differential scanning calorimetry (DSC) or microcalorimetry.

The presence of all the active ingredients in the microparticles could be detected by methods known to the skilled person, such as Raman spectroscopy and solid state CP-MAS $^{13}$C NMR spectroscopy.

As reported above, the microparticles of the present invention are physically stable upon storage for at least one month at room temperature and 60% relative humidity.

However, in the case of amorphous or partially amorphous microparticles, further stabilization of the amorphous state can be achieved with the aid of suitable excipients in the relevant pharmaceutical formulation for inhalation.

Suitable excipients include, but are not limited to, mannitol, trehalose, glycine, leucine, and lactose.

Accordingly, in another aspect, the present invention provides a pharmaceutical formulation for administration by inhalation comprising the microparticles of the invention. Said microparticles may be formulated together with one or more pharmaceutically acceptable excipients, additives, diluents or carriers.

For example, the formulation may be provided in the form of suspension in a propellant as aerosol carrier to be administered by pressurized meted dose inhalers (pMDI).

The pMDI comprises a canister wherein the formulation is filled and a metering valve for delivering a daily therapeutically effective dose of the formulation.

In certain embodiments, the aerosol carrier may consist of a non-chlorofluorocarbon-based propellant such as hydrofluoralkane (HFA).

In particular, the propellants HFA 134a, and HFA 227 or mixtures thereof may be advantageously used.

The suspension formulation may comprise additional excipients selected from the group including, but not limited to, surfactants, and wetting agents.

In a preferred embodiment, the formulation is provided in the form of dry powder for inhalation, more preferably in the form of an interactive or ordered mixture, by diluting the microparticles of the invention in a pharmacologically inert physiologically acceptable excipient consisting of coarser particles.

Advantageously, said powder formulation for inhalation may comprise the particles according to the present invention and coarse particles of a physiologically acceptable excipient, e.g. particles having a MD higher than 100 microns. Advantageously, the MD could be from 100 microns to 500 microns, more preferably from 150 to 400 microns, even more preferably from 210 to 355 microns. In another embodiment, the coarse particles have a MD of from 90 to 150 microns.

In one of the preferred embodiments, when their MD is from 210 to 355 microns, the coarse excipient particles have preferably a relatively highly fissured surface.

The "relatively highly fissured" coarse particles can be defined in terms of fissure index and/or rugosity coefficient as described in WO 01/78695 and WO 01/78693, which are incorporated herein by reference in their entireties, and they could be characterized according to the description therein reported. Advantageously, the fissure index of said coarse particles is of at least 1.25, preferably of at least 1.5, more preferably of at least 2.0, while the rugosity coefficient is of at least 1.25.

Preferably the afore-mentioned powder formulation may further comprise a fraction of fine particles having a MMD lower than 35 microns preferably lower than 15 microns, more preferably lower than 10 microns, composed of particles of a physiologically acceptable excipient and particles of an additive material selected from the class of the anti-adherents such as the amino acids leucine and isoleucine or of the lubricants such as magnesium stearate, sodium stearyl fumarate stearyl alcohol, stearic acid and sucrose monopalmitate (hereinafter the pre-blend fraction).

The physiologically acceptable excipient may be constituted of any amorphous or crystalline physiologically acceptable pharmacologically-inert material of animal or vegetal source or combination thereof. Preferred materials are crystalline sugars and for example monosaccharides such as glucose or arabinose, or disaccharides such as maltose, saccharose, dextrose or lactose. Polyalcohols such as mannitol, sorbitol, maltitol, lactitol may also be used. The most preferred material is α-lactose monohydrate.

Examples of commercial lactose are Capsulac™, Inhalac™, and Pharmatose™.

An example of commercial mannitol is Pearlitol™.

In a preferred embodiment, the fraction of fine particles is composed of 98% by weight of α-lactose monohydrate and 2% by weight of magnesium stearate and the ratio between the fraction of fine particles and the fraction of coarse particles made of α-lactose monohydrate particles is 10:90% by weight, respectively.

The amount of magnesium stearate in the final formulation is advantageously from 0.02% to 1.0% by weight on the total weight of the formulation, preferably from 0.05 to 0.5% by weight, more preferably from 0.1 to 0.4% by weight, even more preferably from 0.2 to 0.3% by weight.

The powder formulation for inhalation comprising the microparticles according to the present invention is endowed with good flowability properties and is characterized by a high degree of homogeneity. In fact, after the mixing, the content uniformity of the active ingredient, expressed as relative standard deviation (RSD), is equal to or lower than 5%, preferably equal to or lower than 3.5%.

Said powder formulation may be administered by inhalation with any type of DPIs known in the art.

DPIs can be divided into two basic types: i) single dose inhalers, for the administration of pre-subdivided single doses of the active compound; and ii) multidose dry powder inhalers (MDPIs), either with pre-subdivided single doses or pre-loaded with quantities of active ingredient sufficient for multiple doses. On the basis of the required inspiratory flow rates (l/min) which in turn are strictly depending on their design and mechanical features, DPIs are divided into:

i) low-resistance devices (>90 l/min);

ii) medium-resistance devices (about 60 l/min); and iii) high-resistance devices (about 30 l/min).

The dry powder formulations comprising the microparticles of the present invention are particularly suitable for multidose DPIs comprising a reservoir from which individual therapeutic dosages can be withdrawn on demand through actuation of the device.

Other multidose devices that may be used are, for instance, the DISKUS™ of GlaxoSmithKline, the TURBOHALER™ of AstraZeneca, the TWISTHALER™ of Schering, and the CLICKHALER™ of Innovata.

As marketed examples of single dose devices, there may be mentioned ROTOHALER™ of GlaxoSmithKline, HANDIHALER™ of Boehringer Ingelheim, Breezehaler™ of Novartis, and Monodose RS01 of Plastiape.

In a preferred embodiment, the dry powder formulation is filled in the DPI device disclosed in WO 2004/012801, which is incorporated herein by reference in its entirety, being particularly suitable for the delivery of an extrafine formulation.

To protect the DPI from ingress of moisture into the formulation, it may be desirable to overwrap the device in a flexible package capable of resisting moisture ingress such as that disclosed in EP 1 760 008, which is incorporated herein by reference in its entirety.

The microparticles of the present invention are indicated for the prevention and/or treatment of inflammatory or obstructive airways diseases such as asthma and chronic obstructive pulmonary disease (COPD).

Other respiratory disorders characterized by obstruction of the pheripheral airways as a result of inflammation and/or presence of mucus, such as chronic obstructive bronchiolitis, bronchiectasies, and cystic fibrosis, may also benefit by their use.

In certain embodiments, the microparticles of the present invention are particularly suitable for the prevention and/or treatment of severe and/or very severe forms of respiratory disorders, in particular severe and/or very severe forms of COPD.

When the microparticles are administered by inhalation, it is preferred that the dosage of the beclometasone dipropionate, based on the anhydrous form of beclometasone dipropionate (BDP), administered is 25 microg to 400 microg, preferably 50 microg to 200 microg; more preferably 100 microg or 200 microg per actuation; and that the dosage of the salt of formoterol, based on dihydrate fumarate salt of formoterol (FF), administered is 3 microg to 24 microg, preferably 6 microg or 12 microg per actuation; and that the dosage of the salt of glycopyrronium, based on the bromide salt of glycopyrronium (GB), administered is 10 microg to 63 microg, preferably 12.5 microg or 25 microg per actuation.

Other features of the invention will become apparent in the course of the following descriptions of exemplary embodiments which are given for illustration of the invention and are not intended to be limiting thereof

EXAMPLES

Example 1

Manufacture of the Microparticles According to the Present Invention 15 g of a mixture of formoterol fumarate dihydrate (FF), beclometasone dipropionate (BDP) and glycopyrronium bromide (GB) in a 84.4:10.5:5.1% weight ratio was dissolved in 1500 ml of 90:10% v/v ethanol:water. The feedstock solution was spray dried using a B290 bench top spray dryer (Buchi) with a 2-fluid nozzle at a feed rate of 5 g $min^{-1}$. The spray drying parameters are reported in Table 1.

TABLE 1

| Parameter | Setting |
|---|---|
| Inlet temperature (° C.) | 125 |
| Outlet temperature (° C.) | 83 |
| Atomisation air pressure (mm) | 35 (~414 L $h^{-1}$) |
| Aspirator setting (%) | 90 (~30-35 $m^3$ $h^{-1}$) |
| Filter pressure (mbar) | 30 |

After completion of the spray drying, the cyclone and collection vessel were separated from the B290 spray dryer and stored for 24 hours at a temperature of 25° C. and at a relative humidity of 20%. A flowable powder was recovered with a yield of 77% (11.7 g).

Example 2

Characterization of the Microparticles of the Present Invention

The microparticles as obtained in Example 1 were characterized in terms of drug content, particle size, morphology, physical state, cohesion/adhesion forces and specific surface area.

Drug Content.

It was determined by UPLC assay (mean±SD; n=5). The results are reported in Table 2, indicating that it is within ±3% of the target concentration for each active ingredient (API) in the spray dried powder.

TABLE 2

| API | Actual concentration (% w/w) | Theoretical concentration (% w/w) |
|---|---|---|
| BDP | 82.0 ± 0.3 | 84.4 |
| GB | 10.6 ± 0.1 | 10.5 |
| FF | 5.1 ± 0.0 | 5.1 |

Particle Size.

The particle size was determined by laser diffraction using an R1 lens (Sympatec HELOS). A sample of the powder was dispersed for two measurement conditions using an air pressure of 0.5 and 3 bar respectively (Sympatec RODOS) and sampled at a rate of 5 m/s from a controlled temperature and humidity dosing unit (Sympatec ASPIROS). The average d[v,10], d[v,50], d[v,90] values were calculated from triplicate measurements. The span was calculated using the following equation:

$$Span=[d(v,0.9)-d(v,0.1)]/d(v,0.5)$$

The values obtained for particle size, which are reported in Table 3, were not affected by the dispersion pressure, indicating a free flowing powder with no hard aggregates.

TABLE 3

| Dispersion pressure (bar) | d[v, 10] | d[v, 50] | d[v, 90] | Span |
|---|---|---|---|---|
| 0.5 | 0.20 (±0.01) | 1.83 (±0.06) | 3.72 (±0.07) | 1.92 |
| 3.0 | 0.20 (±0.01) | 1.76 (±0.05) | 3.50 (±0.04) | 1.88 |

Morphology.

The morphology of the microparticles was determined by scanning electron microscope (SEM) using Jeol JSM-6480LV instrument. Samples were mounted on carbon tape and stored in a vacuum for 12 hours prior to analysis to prevent outgassing. Each sample was sputter coated with gold before imaging.

The shape factor analysis was performed as follows. A sample of spray dried powder was dispersed on a 10 mm circular glass coverslip and coated with gold using an Agar sputter coater. SEM micrographs were obtained using a LEO1430VP SEM at an accelerating voltage of 10 kV and working distance of 10 mm. 120 SEM micrographs were acquired at 0° tilt and analyzed using Image Pro Analyser Version 7.0. The measurement parameters were set to acquire individual particles for shape analysis and any sampling anomalies i.e. selection of multiple particles, were removed manually. The roundness factor (RN) was determined using the equation $RN=p2/4\pi A$, where p is the perimeter and A is the area. Particle Shape factor (PSF) was calculated from the roundness factor using the equation $PSF=1/RN$. Statistical analysis was performed on the RN and PSF data to determine whether sufficient particles had been analyzed to give consistent data. The powder exhibited a uniform spherical morphology as demonstrated by SEM pictures (FIG. 1). Both the roundness (RN) and particle shape factor determined by image analysis of 3953 individual particles confirmed the spherical morphology of the particles (see Table 4).

TABLE 4

| | Roundness | Particle shape factor |
|---|---|---|
| Mean | 1.008 | 0.993 |
| S.D. | 0.039 | 0.028 |
| Median | 1.000 | 1.000 |
| N | 3953 | 3953 |

Physical State.

It was investigated by X-ray powder diffraction (XRPD) and Differential scanning calorimetry (DSC). XRPD was performed using a Bruker AXS D8 Advance, equipped with a Vantec-1 detector and using Cu K-alpha radiation (1.54 A). As for DSC, the heat flow ($W g^{-1}$) as a function of increasing temperature (° C.) was determined using a TA Instruments Q2000 instruments. Samples were weighed into a non-hermetic aluminum DSC pan. The samples were equilibrated at 20° C. before the temperature was ramped 5° C. $min^{-1}$ up to 220° C. The analysis was performed in triplicate and interpreted using Universal Analysis software.

Both DSC and XRPD indicate that the material is amorphous. In fact, compared to the reference materials, the spray dried microparticles exhibited no peaks corresponding to short range order and crystalline structure and a typical amorphous halo is seen. No melting point was identifiable in the DSC trace.

Cohesion/Adhesion Forces.

The force measuring capabilities of the atomic force microscope (AFM) were used to directly measure the adhesion forces between two surfaces. Tipless contact mode AFM cantilevers (Bruker) with calibrated spring constant (typically 0.2-0.4 $Nm^{-1}$) were used for all adhesion-cohesion measurements. Probes were prepared by attaching the microparticles to the tip of the cantilever, which was confirmed by optical and variable pressure SEM before use. A bed of the spray dried microparticles or Inhalac 50 lactose was fixed onto a silicon substrate using a thin layer of glue. Force-distance curves were recorded by monitoring the deflections of the cantilever as the probe and sample were brought into contact (approach trace), and then separated (retract trace). Cohesion/adhesion data was obtained from the microparticles and lactose samples consecutively with the same tip. Data was obtained in a 5×5 grid with 500 nm spacing. Each grid generates 25 force curves over a 2×2 µm area. The experiment was repeated with a different particle probe or different sampling area. All experiments were conducted at ambient environmental conditions. A total of 153 cohesion and 144 adhesion force curves were acquired and processed to extract the interaction force (nN).

Comparison of the obtained adhesion and cohesion forces suggests that there is no statistical difference in the magnitude of the interaction of the microparticles of the invention with themselves or with the lactose powder. In sharp contrast, common micronized active ingredients are either strongly adhesive or cohesive. In view of said properties, the microparticles of the present invention may exhibit improved dispersion when formulated as interactive ordered mixtures with excipient particles of lactose as a carrier. In fact, they would be less prone to give rise to the formation of stable agglomerates like common micronized active ingredients.

Specific Surface Area.

The specific surface area of was determined using nitrogen multipoint BET (Brunauer-Emmet-Teuer) with a TriStar II 3020 instrument. The values are reported in Table 5.

TABLE 5

| | BET surface area ($m^2 g^{-1}$) | Total volume of pores <3063.514 Å ($cm^3 g^{-1}$) | BJH adsorption average pore diameter (Å) |
|---|---|---|---|
| Run 1 | 2.6120 | 0.004248 | 6.0434 |
| Run 2 | 2.3339 | 0.004556 | 5.9286 |
| Run 3 | 2.5183 | 0.004104 | 6.1602 |
| Mean | 2.488 | 0.004 | 6.044 |
| S.D. | 0.14 | 0.00 | 0.12 |

Example 3

Dry Powder Formulation Comprising the Microparticles of the Present Invention

A hard pellet carrier containing coarse lactose (sieve fraction 212-355 µm) and co-micronized pre-blend in a ratio of 9:1 was prepared, before the manufacture of the formulation, according to the teaching of WO 01/78693, which is incorporated herein by reference in its entirety. Briefly, alpha-lactose monohydrate particles (sieve fraction 212-355 µm) and a pre-blend fraction of alpha-lactose monohydrate and magnesium stearate were mixed in a ratio of 9:1.

A powder formulation (50 g batch size) containing 1.22% w/w of the microparticles of Example 1, equivalent to 100 µg BDP, 12.5 µg GB, and 6.0 µg FF in 10 mg dose, was prepared in a Turbula mixer. It was prepared by separately weighing out the hard pellet carrier and the microparticles. Half the carrier was added to a stainless steel vessel followed by the microparticles. The remaining carrier was added and the contents mixed at 32 rpm for 90 minutes. The formulation was then sieved using a 500 µm sieve and mixed for a further 30 minutes at 32 rpm. The formulation was stored in an amber glass jar for a minimum of 24 hours at 20° C. an 40% relative humidity prior to further analysis.

Example 4

The powder formulation of Example 3 was characterized in terms of the uniformity of distribution of the active ingredients and aerosol performances after loading it in the multidose dry powder inhaler described in WO 2004/012801, which is incorporated herein by reference in its entirety, and quoted hereinafter as NEXThaler®.

Uniformity of Distribution.

About 10 mg of the formulation was weighed directly into a 25 mL volumetric flask. It was sampled 10 times. The flask was made up to volume with 60:40% v/v MeOH:$H_2O$ and sonicated for 2 minutes. The samples were analyzed for each active ingredient using UPLC-PDA assay. The results (mean value±RSD) are reported in Table 6.

TABLE 6

| Drug | Content (μg 10 $mg^{-1}$) | RSD (%) | % of Target |
|---|---|---|---|
| BDP | 98.75 ± 1.23 | 1.25 | 98.75 |
| GB  | 12.64 ± 0.18 | 1.45 | 105.37 |
| FF  | 6.08 ± 0.08  | 1.24 | 101.27 |

Aerosol Performances.

Aerosol performances were determined using the Next Generation Impactor (NGI) with a USP induction port and pre-separator containing 15 mL 60:40% v/v MeOH:$H_2O$. Critical flow ($P_3/P_2$ ratio) was <0.5 at the sampling flow rate of 60 L/min. The aerodynamic particle size distribution was based on 5 actuations from the NEXThaler®, each sampled into 4 liters of air (equivalent to an inhalation time of 4 s). The device was weighed before and after each actuation to determine the shot weight (mg). A minimum of 1 minute was allowed between consecutive actuations to allow static charge to dissipate.

Samples were collected from the NGI using a fixed volume technique. MeOH:$H_2O$ (60:40% v/v) was dispensed into the induction port (including mouthpiece); pre-separator; and each stage using an electronic metering dispenser. The induction port (30 mL) and pre-separator (50 mL) were sealed using silicone bungs and shaken by hand for 2 minutes before the samples were collected. The NGI stages (10 mL stages 1-2; 15 mL stage 3-MOC) were rocked using a NGI rocker for 3 minutes. All samples were filtered using a 0.2 μm syringe filter before analysis by UPLC-PDA.

The following parameters, were calculated: i) the delivered dose (DD) which is the amount of drug delivered from the device recovered in all the parts of impactor; ii) the fine particle mass (FPM) which is the amount of delivered dose having a particle size equal to or lower than 5.0 micron iii) the fine particle fraction (FPF) which is which is the ratio between the fine particle mass and the delivered dose; iv) the MMAD±GSD; and v) the extrafine FPF which is the percentage of the fine particle mass having a particle size equal to or lower than 2.0 micron and/or equal to or lower than 1.0 micron. The results (mean value±S.D, n=6) are reported in Table 7.

From the data of Tables 6 and 7, it can be appreciated that the prepared formulation shows both an excellent homogeneity with RSD values <2% and high delivered dose and respirable fraction (FPF) for all the three active ingredients. The formulations also give rise to a fraction of particles having a diameter equal or lower than 2 microns higher than 35% and a fraction of particles having a diameter equal to or lower than 1 micron higher than 20% for all the active ingredients. This confirms that it could be suitable for the prevention and/or treatment of the diseases affecting the distal tract of the respiratory tree.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. Multicomponent microparticles, for use in a formulation for inhalation, each microparticle comprising a combination of beclometasone dipropionate, formoterol fumarate, and glycopyrronium bromide as active ingredients in a weight ratio of 35:15:45 to 94:1:5 w/w/w, wherein said microparticles have a shape factor of from 0.80 to 1.15, and wherein said microparticles are obtained by a process comprising:
   a) preparing a solution of said beclometasone dipropionate, formoterol fumarate, and glycopyrronium bromide in a pre-determined ratio in a solvent consisting of a mixture of ethanol:water in a ratio of from 85:15 to 95:5 v/v;
   b) generating an aerosol from said solution, to obtain atomized droplets;
   c) drying said atomized droplets to yield the microparticles; and
   d) isolating said microparticles.

2. Microparticles according to claim 1, which have a shape factor of from 0.95 to 1.05.

3. Microparticles according to claim 1, wherein at least 90% of all said microparticles have a volume diameter equal to or lower than 6.0 microns, and the volume median diameter of said microparticles is from 1.0 to 3.0 microns.

4. Microparticles according to claim 2, wherein at least 90% of all said microparticles have a volume diameter equal to or lower than 6.0 microns, and the volume median diameter of said microparticles is from 1.0 to 3.0 microns.

5. Microparticles according to claim 1, wherein each of said beclometasone dipropionate, formoterol fumarate, and glycopyrronium bromide is present in an amorphous form.

TABLE 7

|     | DD (μg)     | FPM (μg)    | FPF (%)    | MMAD (μm)  | FPF < 1 μm  | FPF < 2 μm  |
|-----|-------------|-------------|------------|------------|-------------|-------------|
| FF  | 5.2 ± 0.1   | 3.7 ± 0.2   | 70.2 ± 3.0 | 1.9 ± 0.1  | 21.6 ± 1.0  | 39.7 ± 1.1  |
| GB  | 11.5 ± 0.4  | 7.9 ± 0.5   | 68.5 ± 3.7 | 1.9 ± 0.1  | 21.7 ± 0.7  | 39.3 ± 1.6  |
| BDP | 87.6 ± 2.2  | 60.0 ± 3.6  | 68.5 ± 3.1 | 1.9 ± 0.1  | 20.8 ± 0.7  | 38.6 ± 1.2  |

6. A process for preparing microparticles according to claim 5, said process comprising:
  a) preparing a solution of beclometasone dipropionate, formoterol fumarate, and glycopyrronium bromide in a pre-determined ratio in a suitable solvent or mixture thereof;
  b) generating an aerosol of atomized droplets from said solution; and
  c) drying said atomized droplets to yield said microparticles.

7. A process according claim 6, futher comprising:
  d) isolating said microparticles.

8. A process according to claim 6, wherein said solvent consists of a mixture of ethanol:water in a ratio of 85:15 to 95:5 v/v.

9. Microparticles according to claim 1, wherein at least one of said beclometasone dipropionate, formoterol fumarate, and glycopyrronium bromide is in a crystalline form.

10. A process for preparing microparticles according to claim 9, said process comprising:
  a) preparing a solution of beclometasone dipropionate, formoterol fumarate, glycopyrronium bromide in a pre-determined ratio in a suitable solvent or mixture thereof;
  b) generating an aerosol of atomized droplets from said solution;
  c) drying said atomized droplets to yield first microparticles;
  d) collecting said first microparticles in a vessel containing an anti-solvent for all of beclometasone dipropionate, formoterol fumarate, and glycopyrronium bromide;
  e) applying a high intensity ultrasound to change the morphology of said first microparticles and induce crystallization to obtain second microparticles; and
  f) isolating said second microparticles.

11. A process according to claim 10, wherein said anti-solvent is selected from the group consisting of n-heptane, cyclohexane, and a fluorinated hydrocarbon.

12. A process according to claim 11, wherein said fluorinated hydrocarbon is perfluorodecalin.

13. A pharmaceutical aerosol formulation, comprising microparticles according to claim 1 in suspension in a liquefied propellant gas.

14. A pressurized metered dose inhaler (pMDI), comprising a canister containing a pharmaceutical aerosol formulation according to claim 13 and a metering valve.

15. A dry powder pharmaceutical formulation, comprising microparticles according to claim 1 and, optionally, a carrier.

16. A dry powder inhaler, containing a dry powder formulation according to claim 15.

17. A method for treatment of an inflammatory and/or obstructive airway disease, comprising administering to a subject in need thereof an effective amount of microparticles according to claim 1.

18. A method according to claim 17, wherein said disease is asthma or chronic obstructive pulmonary disease (COPD).

19. Microparticles according to claim 1, wherein said formoterol fumarate is present in its dihydrate form.

20. Microparticles according to claim 5, wherein said formoterol fumarate is present in its dihydrate form.

21. Microparticles according to claim 9, wherein said formoterol fumarate is present in its dihydrate form.

22. Microparticles according to claim 9, which are obtained by a process comprising:
  a) preparing a solution of beclometasone dipropionate, formoterol fumarate, glycopyrronium bromide in a pre-determined ratio in a suitable solvent or mixture thereof;
  b) generating an aerosol of atomized droplets from said solution;
  c) drying said atomized droplets to yield first microparticles;
  d) collecting said first microparticles in a vessel containing an anti-solvent for all of beclometasone dipropionate, formoterol fumarate, and glycopyrronium bromide; and
  e) applying a high intensity ultrasound to change the morphology of said first microparticles and induce crystallization.

23. Microparticles according to claim 22, wherein said anti-solvent is selected from the group consisting of n-heptane, cyclohexane, and a fluorinated hydrocarbon.

24. Microparticles according to claim 23, wherein said fluorinated hydrocarbon is perfluorodecalin.

* * * * *